US007419264B1

(12) United States Patent
Otten, III et al.

(10) Patent No.: US 7,419,264 B1
(45) Date of Patent: Sep. 2, 2008

(54) OPHTHALMIC ABERROMETER FOR MEASURING ABERRATIONS IN THE EYE

(75) Inventors: Leonard John Otten, III, Placitas, NM (US); Paul Harrison, Albuquerque, NM (US); Gavin Erry, Albuquerque, NM (US)

(73) Assignee: Kestrel Corporation, Albuquerque, NM (US)

( * ) Notice: Subject to any disclaimer, the term of this patent is extended or adjusted under 35 U.S.C. 154(b) by 382 days.

(21) Appl. No.: 10/981,996

(22) Filed: Nov. 4, 2004

Related U.S. Application Data

(60) Provisional application No. 60/518,274, filed on Nov. 7, 2003.

(51) Int. Cl.
*A61B 3/14* (2006.01)
(52) U.S. Cl. ....................... 351/210; 351/211
(58) Field of Classification Search ............... 351/200, 351/205, 210, 211, 221, 206
See application file for complete search history.

(56) References Cited

U.S. PATENT DOCUMENTS 6,595,642 B2 * 7/2003 Wirth ......................... 351/211

FOREIGN PATENT DOCUMENTS

WO    WO 03/002024    1/2003

OTHER PUBLICATIONS

Prieto et al., Analysis of the performance of the Hartmann-Shack sensor in the human eye, J. Opt. Soc. Am, vol. 17, No. 8, Aug. 2000.

\* cited by examiner

*Primary Examiner*—Joseph Martinez
(74) *Attorney, Agent, or Firm*—Janeen Vilven-Doggett; Peacock Myers, P.C.

(57) ABSTRACT

A ophthalmic aberrometer uses a wavefront sensor aligned with an eye under examination through an optical path and a light source for introducing a light beam into the eye via the optical path, wherein the optical path has a reference through which the light beam passes before passing to an eye retina to form a reference spot on the retina, a focus dynamic range extender, and an astigmatism dynamic range extender positioned in the optical path between the reference and an eye under examination. The wavefront sensor is positioned to receive a wavefront reflected from the eye retina via the optical path.

12 Claims, 10 Drawing Sheets

OPHTHALMIC ABERROMETER FOR MEASURING ABERRATIONS IN THE EYE

CROSS REFERENCE TO OTHER APPLICATIONS

This application claims benefit under 35 U.S.C. § 119(e) of provisional application No. 60/518,274, filed Nov. 7, 2003, which is incorporated by reference herein, in its entirety, for all purposes.

STATEMENT REGARDING GOVERNMENT INTEREST

This invention was made with government support under Contract No. 2R44EY12174-02, Contract No. 1R43EY014493-01A1 and Contract No. 1 R43 EY014518-01 awarded by the National Eye Institute. The government has certain rights in the invention.

FIELD OF THE INVENTION

The present invention relates to a novel opthalmic aberrometer and method for measuring aberrations in an eye.

BACKGROUND ART

A human eye is subject to a variety of optical aberrations. Accurate measurement of optical aberrations is essential for precise correction by customized photo-refractive surgery, by use of customized contact lenses, or by use of customized intra-ocular lenses. Wavefront measurement is a commonly used method to determine optical aberrations of an eye, monitoring penetrating keratoplasty (PKP) healing, or providing quantitative error data.

Shack-Hartmann (SH) wavefront systems are known in the art for measuring ocular aberrations. Starting at the retina, an ideal wavefront is generated which passes through the optical path of the eye. As the wavefront exits the eye, it contains a map of the eye's aberrations for analysis by a lenslet array of a SH sensor. A lenslet array dissects the incoming light into a large number of sub-apertures, and then measures the wavefront slope across each sub-aperture. The sensor information is used to analyze the optical properties of the system which created the wavefront of the eye.

SH wavefront sensors suffer from problems with intensity modulation that introduce scintillation effects and non uniformity of retinal reflection. For example, spot shapes on the Hartmannogram are very irregular, which makes the error of estimation of the spots' centers rather large. To overcome this problem, existing systems collect multiple images over time and average the multiple images or collect an image over a long period of time to smooth out the scintillation effects. However, temporal and spatial errors are introduced into the data with these solutions.

Occluded or damaged corneas produce scatter and/or scintillation beyond those found in normal eyes. Scatter and scintillation produce amplitude fluctuation in SH lenslet images rendering a wavefront that is known to be inaccurate. Therefore eyes with larger scatter and/or scintillation are excluded from aberration measurements using existing SH aberrometers. The accuracy and limitations for the SH sensor are discussed by Pedro M. Prieto et al. "Analysis of the performance of the Hartmann-Shack sensor in the human eye" J. Opt. Soc. Am. Vol. 17 No. 8, August 2000, pgs. 1396-1398.

Existing SH wavefront sensors have a narrow dynamic range and suffer from a lack of high sensitivity. Existing SH wavefront systems only work with relatively clear lenses and corneas. Currently, no wavefront system exists that works well to produce objective data for eyes with scintillation and scatter, over a wide dynamic range, or varying amounts of accommodation.

BRIEF SUMMARY OF THE INVENTION

The present invention relates to an improved system and method for measuring aberrations from eyes.

One aspect of the present invention provides an ophthalmic aberrometer comprising a Shack-Hartmann wavefront sensor aligned with an eye under examination through an optical path. A light source is positioned to introduce a light beam into an eye via the optical path. The optical path comprises a point source reference scanner through which the light beam passes before passing to the eye to form a point source reference mark on a retina, a focus dynamic range extender, and an astigmatism dynamic range extender, wherein the focus dynamic range extender and the astigmatism dynamic range extender are positioned in the optical path between the point source reference scanner and the eye. The Shack-Hartmann wavefront sensor is positioned to receive a wavefront reflected from the eye retina via the optical path. A processor is connected to the sensor for processing the wavefront's characteristics.

Another aspect of the present invention provides an ophthalmic aberrometer comprising a distorted grating wavefront sensor aligned with an eye through an optical path. A light source introduces a light beam into the eye via the optical path. The optical path comprises a point source reference scanner through which the light beam passes before passing to the eye retina to form a point source reference spot on the retina, a focus dynamic range extender, and an astigmatism dynamic range extender. The focus dynamic range extender and the astigmatism dynamic range extender are positioned in the optical path between the point source reference scanner and the eye. The distorted grating wavefront sensor is positioned to receive a wavefront reflected from the eye retina via the optical path.

Another aspect of the present invention provides an ophthalmic aberrometer comprising a distorted grating wavefront sensor and a Shack-Hartmann wavefront sensor interfacing with an optical path. A light source is positioned to introduce a light beam into the optical path. The optical path comprises a reference through which a light beam passes before passing to an eye retina, wherein the focus dynamic range extender and the astigmatism dynamic range extender are positioned between the reference and the eye. The distorted grating wavefront sensor and the Shack-Hartmann wavefront sensor are positioned to receive a wavefront reflected from the eye simultaneously via the optical path.

Another aspect of the present invention provides a method for determining aberrations of an eye under examination. A light beam is directed onto a retina of an eye through an optical path. The optical path comprises a point source reference scanner through which the light beam passes before passing to the retina to form a point source reference mark on the retina, a focus dynamic range extender, and an astigmatism dynamic range extender. The focus dynamic range extender and the astigmatism dynamic range extender are positioned between the point source reference scanner and the eye under examination. At least a portion of the light beam is reflected from the retina of the eye under examination through the optical path to a wavefront sensor. One or more dynamic range extenders are adjusted within the optical path to produce a wavefront that falls within a dynamic range of the sensor. The wavefront, which is reflected from the retina via the optical path, is detected on the wavefront sensor. The characteristics of the detected wavefront are determined.

Another aspect of the present invention provides a method for obtaining wavefront aberrations from an eye under examination. A light beam from a light source is directed onto a retina of an eye under examination through an optical path. The optical path comprises a point source reference scanner through which the light beam passes before passing to the eye to form a dithered reference spot on the retina, a focus dynamic range extender, and an astigmatism dynamic range extender. At least a portion of the light beam is reflected from the retina of the eye under examination through the optical path to a wavefront sensor. One or more dynamic range extenders are adjusted to compensate for the eyes defocus and astigmatism thereby bringing the dynamic range to within the dynamic range of the sensor. A variable accommodation mechanism is positioned to introduce into the optical path a virtual target to the eye wherein the apparent position of the virtual target is changed while the eye under examination is focused upon the virtual target.

Another aspect of the present invention provides a method for analyzing aberrations in an eye having frequency signatures of greater than about 15 Hz. The method comprises directing a light beam onto a retina of the eye via an optical path. The optical path comprises a point source reference scanner through which the light beam passes before passing to the eye retina to form a reference spot on the retina, a focus dynamic range extender, and an astigmatism dynamic range extender. At least a portion of the light beam reflected is directed from the retina of the eye via the optical path to a wavefront sensor. At least one of the dynamic range extender is adjusted to adjust the wavefront to fall within the dynamic range of the wavefront sensor. Frequency characteristics of aberrations having frequency signatures greater than about 15 Hz are determined.

Another aspect of the present invention involves the use of a near infrared monochromatic point source reference.

Another aspect of the present invention is improved aberration measurement from one data rendition.

Another aspect of the present invention is improved spatial accuracy for aberrations measured.

Another aspect of the present invention involves the use of variable accommodation optics.

Another aspect of the present invention provides an aberrometer with an improved dynamic range.

Another aspect of the present invention provides an aberrometer with improved specificity.

Another aspect of the present invention involves the use of an aberrometer with an alignment fiduciary for aligning the aberrometer with an eye under examination.

Yet another aspect of the present invention provides an optical aberrometer useful for measuring eyes with occluded lens and corneas.

Yet another aspect of the present invention provides an optical aberrometer for measuring eyes with modest refractive aberrations.

Yet another aspect of the present invention provides an optical aberrometer for imaging eyes with severe refractive aberrations.

Another aspect of the present invention provides an optical aberrometer for measuring eyes under varying accommodation conditions.

BRIEF DESCRIPTION OF THE DRAWINGS

Additional objects and advantages of the present invention will be apparent in the following detailed description read in conjunction with the accompanying drawing figures.

DETAILED DESCRIPTION

Figure 1:
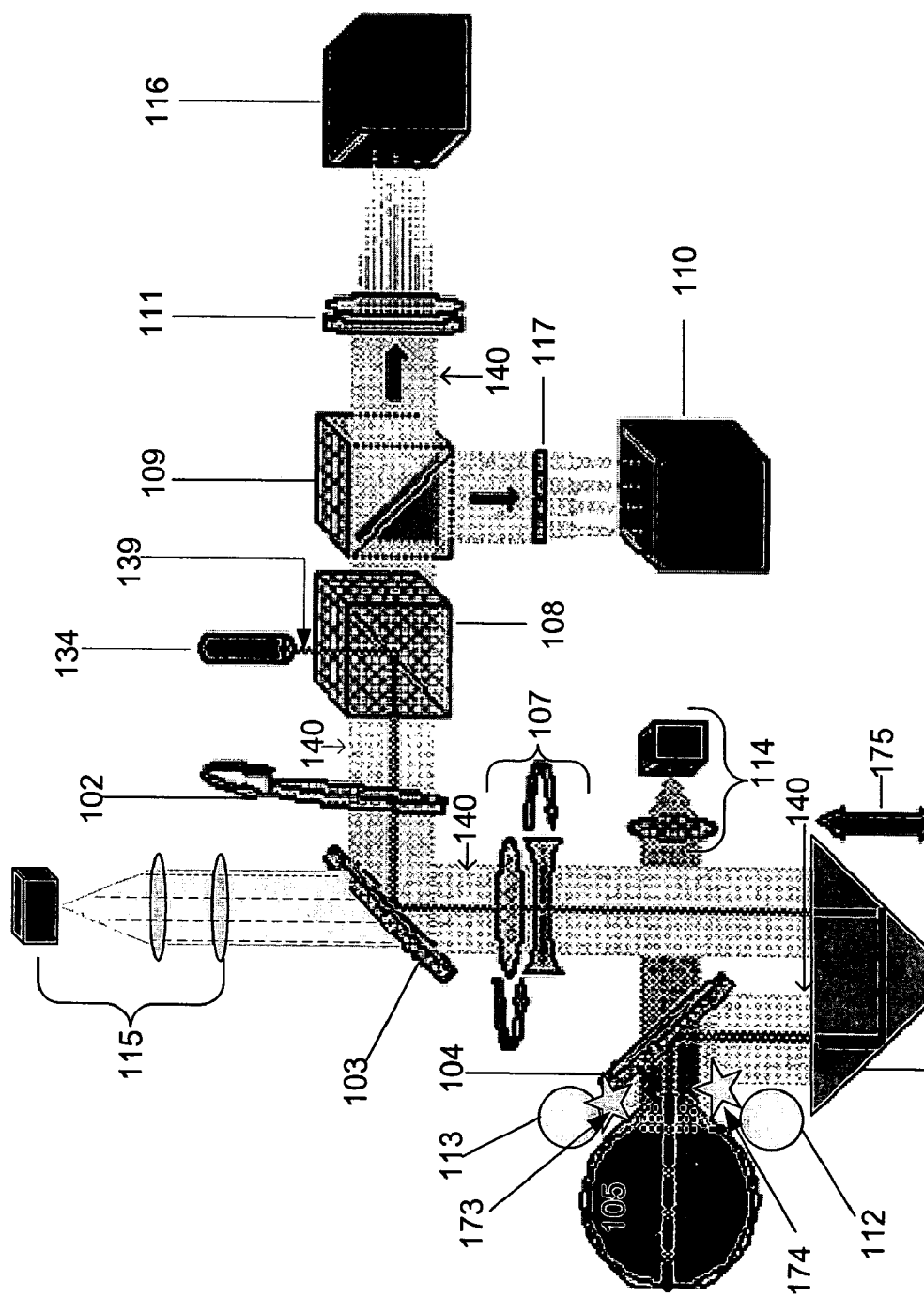
FIG. 1 illustrates an aberrometer according to one embodiment of the present invention.

Although described herein with respect to exemplary embodiments, the present invention is not meant to be so limited, and other modifications and embodiments that fall within the scope of the present invention will be readily apparent to those of skill in the art.

In one embodiment of the present invention, an ophthalmic aberrometer comprises a Shack-Hartmann wavefront sensor aligned with an eye under examination through an optical path. A light source is positioned to introduce a light beam into an eye via the optical path. The optical path comprises a point source reference scanner through which the light beam passes before passing to the eye to form a point source reference mark on a retina. The apparatus further comprises a focus dynamic range extender, and an astigmatism dynamic range extender. The focus dynamic range extender and the astigmatism dynamic range extender are positioned in the optical path between the point source reference scanner and the eye. The Shack-Hartmann wavefront sensor is positioned to receive a wavefront reflected from the eye retina via the optical path. The wavefront's characteristics are processed by a processor connected to the sensor. In a preferred embodiment, the light source is a monochromatic light source. The light source emits a light beam in the about visible to near infrared wavelength. A point source reference scanner can be dithered or static. In a preferred embodiment, the point source reference scanner is dithered. Examples of dithered point source reference scanners are a circular glass wedge and a mirror mounted at a slight angle for introducing a slight angle to the optical axis, but are not limited thereto.

The apparatus further comprises a variable accommodation mechanism which is positioned to introduce a scene into the optical path. For example, the scene is a virtual target wherein the apparent distance of the virtual target is varied and the eye's accommodation to the change in apparent distance is measured.

In another embodiment, an ophthalmic aberrometer comprises a distorted grating wavefront sensor aligned with an eye through an optical path. A light source is positioned for introducing a light beam into the eye via the optical path. The optical path comprises a point source reference scanner through which the light beam passes before passing to the eye retina to form a point source reference spot on the retina, a focus dynamic range extender, and an astigmatism dynamic range extender. The focus dynamic range extender and the astigmatism dynamic range extender are positioned in the optical path between the point source reference scanner and the eye. The distorted grating wavefront sensor is positioned to receive a wavefront reflected from the eye retina via the optical path. In a preferred embodiment, the light source is a monochromatic light source. A point source reference scanner can be dithered or static. In a preferred embodiment, the point source reference scanner is dithered. Examples of point source reference scanners are a circular glass wedge and a mirror mounted at a slight angle for introducing a slight angle to the optical axis, but are not limited thereto.

In addition, an alignment light source is positioned for projecting a fiduciary onto the eye to align the eye with an aberrometer. A near infrared light source is positioned to illuminate the eye with an about near infrared detector. A near infrared signal is detector by a detector detecting in the near infrared range. The pupil in an illuminated eye is measured. For example, a pupil is illuminated with infrared diodes and the illuminated eye is detected with an infrared CCD detector. The width of the pupil is measured without the illuminated eye detecting the illuminating wavelength.

According to another embodiment of the present invention, an ophthalmic aberrometer comprises a distorted grating wavefront sensor and a Shack-Hartmann wavefront sensor interfacing with the optical path. A light source is positioned to introduce a light beam into the optical path. The optical path comprises a reference through which a light beam passes before passing to an eye retina. The focus dynamic range extender and the astigmatism dynamic range extender are positioned between the reference and the eye. A variable accommodation mechanism is positioned to introduce a virtual target into the optical path. The position of the virtual target is changed while the eye under examination is focused upon the virtual target and the eye's accommodation to the apparent change in distance of the virtual target is measured. The distorted grating wavefront sensor and the Shack-Hartmann wavefront sensor are positioned to receive a wavefront reflected from the eye simultaneously via the optical path.

According to another embodiment of the present invention, an ophthalmic aberrometer comprises a Shack-Hartmann wavefront sensor and a distorted grating wavefront sensor aligned with an eye through an optical path. A light source is positioned to introduce a light beam into eye via the optical path. The optical path comprises a reference through which the light beam passes before passing to an eye retina, a focus dynamic range extender, and an astigmatism dynamic range extender. The focus dynamic range extender, and the astigmatism dynamic range extender are positioned between the point source reference scanner and the eye. The Shack-Hartmann wavefront sensor and the distorted grating wavefront sensor are positioned to receive the wavefront reflected from the eye retina simultaneously via the optical path. A variable accommodation mechanism is positioned to introduce a virtual target into the optical path. The position of the eye examination target is changed while the eye under examination is focused upon the eye examination target. An alignment light source is positioned to project a fiduciary onto the front of the eye. A near infrared light source is positioned to illuminate an eye with a near infrared wavelength. The illuminated eye is detected with a near infrared detector and the pupil size is measured.

Another embodiment of the present invention is a method for determining aberrations of an eye under examination. The method comprises directing a light beam onto a retina of an eye through an optical path. At least a portion of the reflected light beam from the retina of the eye under examination is directed through the optical path to a wavefront sensor. One or more dynamic range extenders are adjusted within the optical path to produce a wavefront that falls within a dynamic range of the sensor. A wavefront which is reflected from the retina via the optical path is detected on the wavefront sensor. The characteristics of the wavefront detected are determined.

The method further comprises projecting a fiduciary onto the center of an iris to align the eye with an aberrometer and a detector for detecting the fiduciary on the eye. For example, a light source for projecting the fiduciary onto the center of the iris emits light in the about infrared wavelength, preferably near infrared wavelength. The fiduciary is detected with an infrared detector.

The method further comprises illuminating the eye with a near infrared light source. The illuminated eye is detected with a near infrared detector. The pupil size of the eye is measured and the measurement is considered during analysis of the aberrations measured.

The method further comprises varying the apparent distance of a virtual target introduced into the optical path by a scene generator of a variable accommodation mechanism. The apparent distance of the virtual target is changed while the eye under examination is focused upon the virtual target. The eyes varying accommodation to the moving target is measured.

According to one embodiment a method for analyzing aberrations in an eye having aberration frequencies greater than about 15 Hz with an aberrometer comprises directing a light beam onto a retina of the eye via an optical path. The optical path comprises a dithered point source reference scanner through which the light beam passes before passing to the eye retina to form a dithered reference spot on the retina, a focus dynamic range extender, and an astigmatism dynamic range extender. At least a portion of the light beam reflected from the retina of the eye is directed via the optical path to a wavefront sensor. At least one of the dynamic range extenders is adjusted. The frequency characteristics of aberrations having frequency signatures greater than about 15 Hz is determined.

Referring now to FIG. 1, an aberrometer is illustrated according to one embodiment of the present invention. The aberrometer consists of alignment light sources 112, 113, positioned on either side of an eye 105 for providing a fiduciary to the eye. A detector and optics 114 is aligned with the eye and detects the fiduciary projected onto the front of the eye 105 by the alignment light sources 112, 113. The fiduciary aids in aligning the eye 105 in the appropriate position in relation to the aberrometer. Measurement light sources 173, 174 are positioned on either side of the eye 105 for illuminating the eye. The detector and optics 114 detects the illuminated eye, and the size of the pupil is measured under illuminating conditions that are non-visible to the eye. For example, the light sources 112, 113, 173, 174 emit light in the near infrared wavelengths, and the detector 114 detects in the near infrared range. Alternatively, a single pair of diodes perform the functions of light sources 112, 113, 173, 174.

A focus dynamic range extender 106 is positioned on a moveable platform (not shown) whose position changes in the direction as shown by an arrow 175. An astigmatism dynamic range extender 107 is positioned between the focus dynamic range extender 106 and a light source 134. A light beam 139 from a light source source 134 is introduced into an optical path 140 via a polarizing beam splitter 108. The wavelength of the light beam is determined by the user and is of any safe wavelength. For example, the wavelength is selected from the near infrared range and those wavelengths visible to the eye under examination. Alternatively, the light beam is in the near infrared range and not visible to the eye under examination. The light beam (also know as the point source of light or point source reference) passes through a point source reference scanner 102, an astigmatism dynamic range extender 107, and the focus dynamic range extender 106, before reaching the retina of the eye 105. A percentage of the reference light is reflected back from the retina as a wavefront and expanded and relayed by optics 104 through the focus dynamic range extender 106, an astigmatism dynamic range extender 107, off of chromatic beam splitter 103 which reflects the wavefront and transmits any light from the variable accommodation mechanism comprising a scene generator 115 and associated optics. The wavefront passes through the point source reference scanner 102 and the polarized beam splitter 108 where the polarized light is transmitted to a Shack-Hartmann wavefront sensor and a distorted grating wavefront sensor. A Shack Hartmann wavefront sensor comprises a lenslet array and associated optics 117 and a detector 110. A distorted grating wavefront sensor comprises a distorted grating and associated optics 111 and a detector 116. The wavefront sensors interface with the optical path through, for example, a beam splitter 109 that splits the light between the two sensors. The amount of light sent to each sensor is determined by the sensor's requirements. The point source reference scanner 102 is, for example, a rotating wedge. The eye and a wavefront sensor are connected via optical path for example 140. However, the aberrometer is not limited to the optical path that is illustrated as other optical path layouts will be apparent to persons of ordinary skill in the art.

Figure 2:
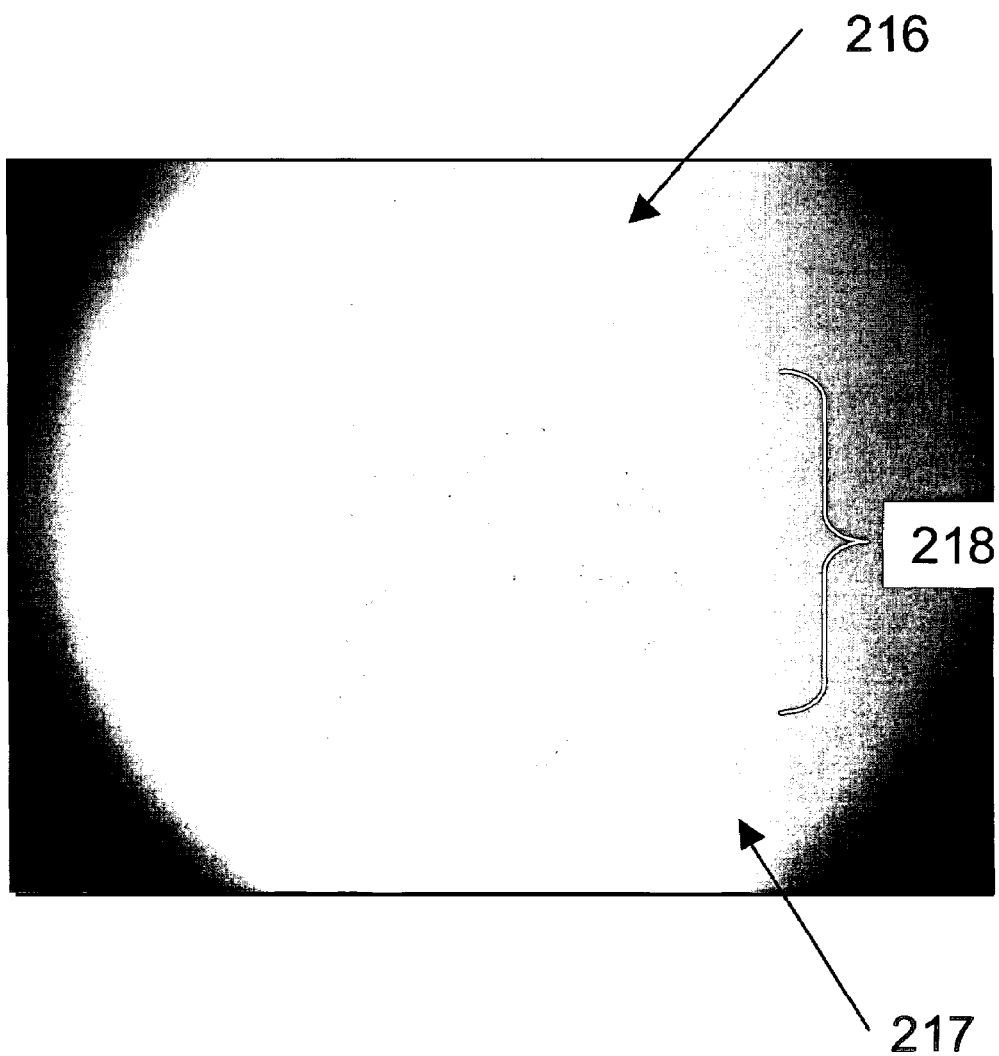
FIG. 2 illustrates an alignment target as seen on the front of the eye according to one embodiment of the present invention.

Referring now to FIG. 2, an alignment fiduciary as seen on the front of the iris of the eye 218 is illustrated according to one embodiment of the present invention. Light sources (not shown) project an alignment fiduciary onto the front of the subject's eye. A light source emits light in the visible to near infrared wavelengths. In a preferred embodiment, the light source emits near infrared light that is not visible to the human eye. The light source is positioned on the aberrometer at either side of the eye input such that the light source beams overlap only when the subject is the correct distance from the aberrometer thereby forming a fiduciary. The light source projects, for example, a circle with a V shape 216 the V being inverted in one beam relative to the other 217. When the beams overlap, they form a circle with a cross in the center (not shown). When the cross is centered on the subject's eye, the subject is positioned correctly relative to the aberrometer.

Figure 3:
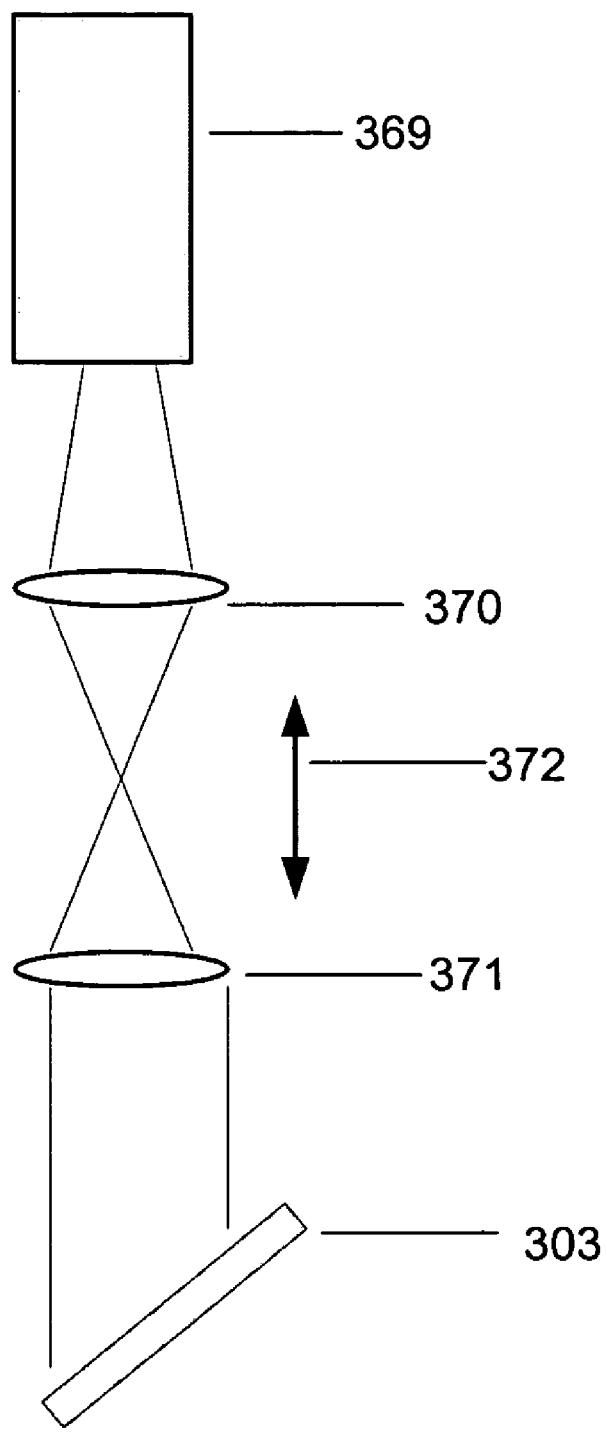
FIG. 3 illustrates a variable accommodation mechanism according to one embodiment of the present invention.

Referring now to FIG. 3, a diagram of a variable accommodation mechanism is illustrated according to one embodiment of the present invention. A virtual target is created electronically via a scene generator 369. The virtual target is located at an equivalent distance of between about 20 cm and infinite distance from the eye. A scene generator 369 projects a scene through a set of lenses 370, 371 that are adjusted relative to one another in the direction indicated by the arrow at 372. A provided image such as a virtual target appears to be at variable distances from an eye observing the target. An image is passed through chromatic beam splitter 303 presenting the virtual target to an eye under examination via the optical path. The wavelength of the scene generator is selected by the user. In a preferred embodiment, the wavelength selected is the about green wavelength. Chromatic beam splitter 303 reflects the reflected reference light from the retina and transmits the bandwidth of the scene generator 369.

Figure 4:
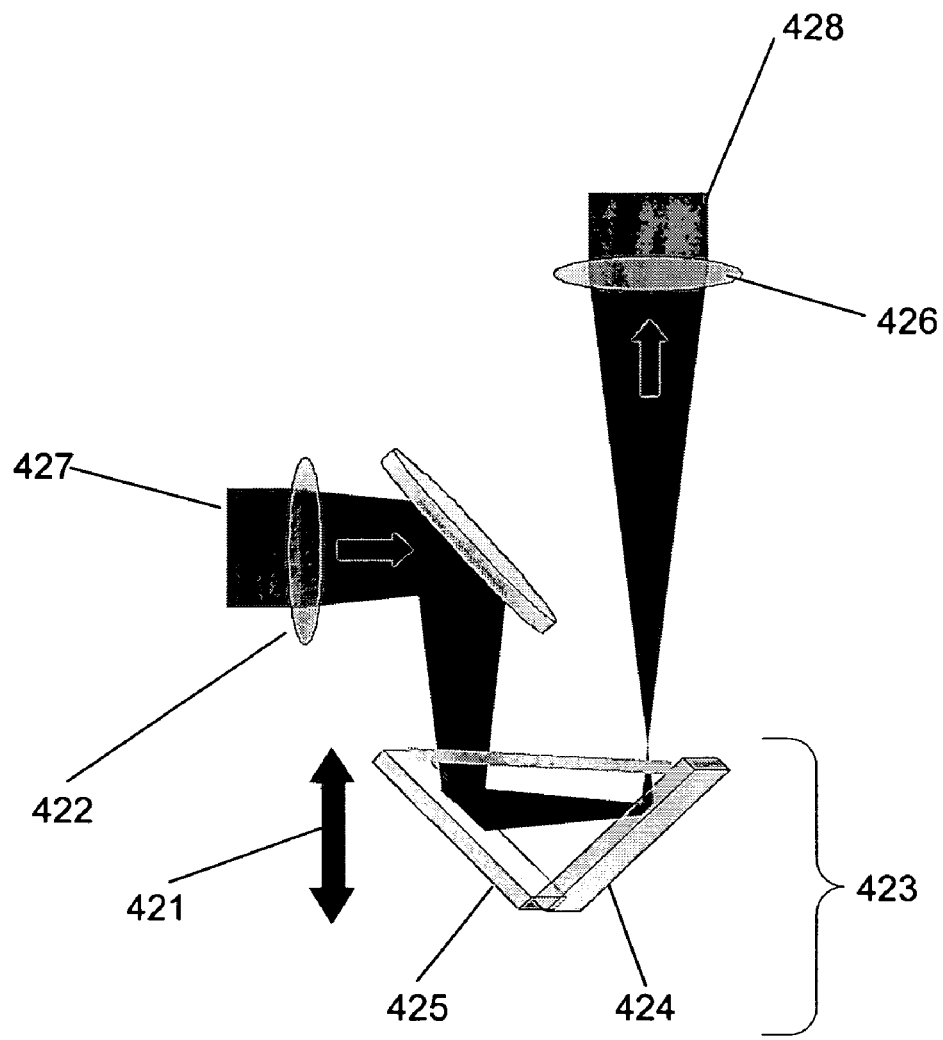
FIG. 4 illustrates a focus dynamic range extender according to one embodiment of the present invention.

Referring now to FIG. 4, a focus dynamic range extender that compensates for variable amounts of ophthalmic defocus in eyes is illustrated according to one embodiment of the present invention. A prism 423 with two internal reflecting surfaces 424, 425 is located on a moving stage (not shown). The prism is located between two lenses 422, 426 that form a 1:1 relay in the system using the reference light reflected from the back of the retina 427. When the prism is translated in the direction indicated by the arrow 421, the optical path length between the two lenses 422, 426 changes, thus introducing a defocus into the wavefront 428 returned from the eye. Compensating for the eye's defocus while measuring aberrations extends the dynamic range of the system without sacrificing a wavefront sensor's sensitivity, (the smallest change in the wavefront that the wavefront sensor can measure).

Figure 5:
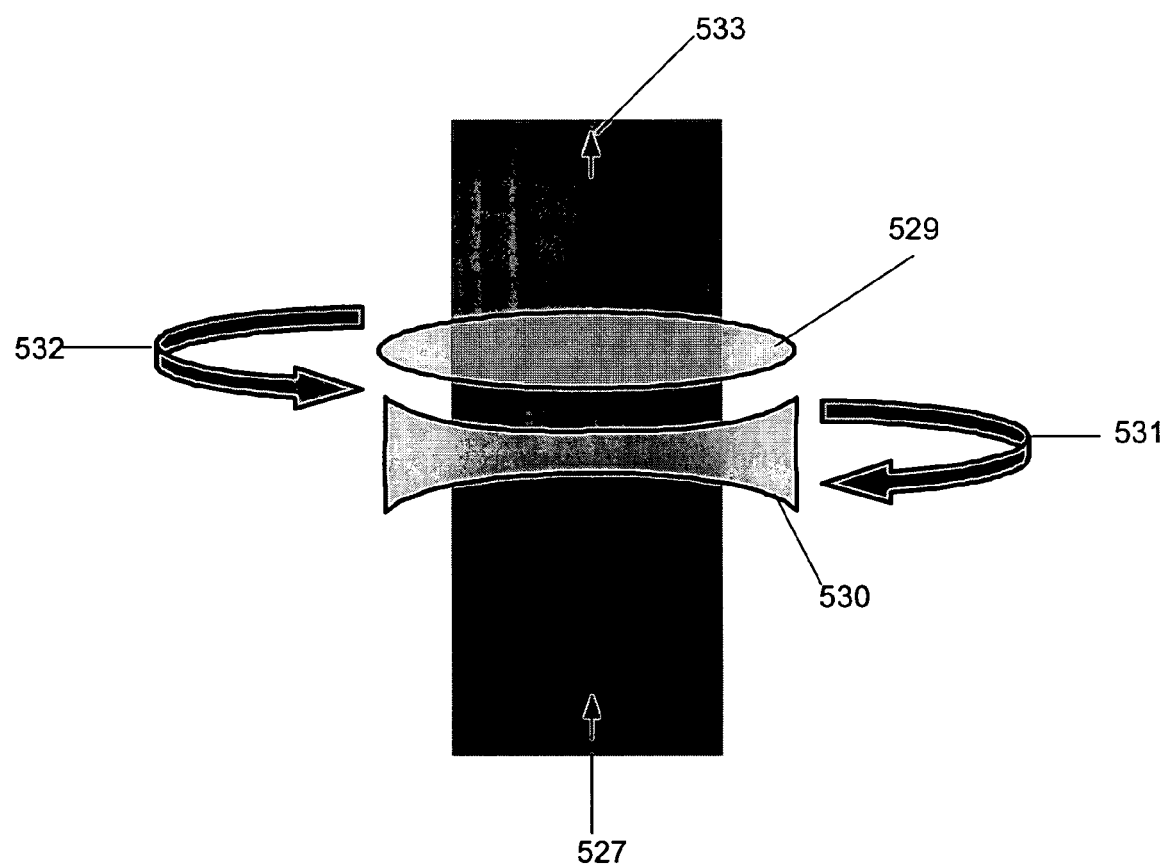
FIG. 5 illustrates an astigmatism dynamic range extender according to one embodiment of the present invention.

Referring now to FIG. 5, an astigmatism dynamic range extender is illustrated according to one embodiment of the present invention. A pair of cylinder lenses 529, 530 are rotated relative to each other and about the optic axis of the aberrometer as indicated by arrows 531, 532. Cylinder lenses 529, 530 have equal but opposite focal length. In a preferred embodiment, lenses 529, 530 are accurately matched. When cylinder lenses 529, 530 are co-aligned, no astigmatism is introduced into the beam. When one lens is rotated relative to the other, the amount of astigmatism introduced into the beam increases. The angle of the astigmatism can be varied by rotating both cylinder lenses in the same direction. An incoming wavefront 527 is modified by an astigmatism dynamic range extender which introduces a known amount of astigmatism correction such that the outgoing wavefront 533 will have an astigmatism that is now within the dynamic range of the wavefront measuring sensors. Compensating for the eye's astigmatism while measuring aberrations, extends the dynamic range of the system without sacrificing a wavefront sensor's sensitivity, (the smallest change in the wavefront that the wavefront sensor can measure.)

Figure 6:
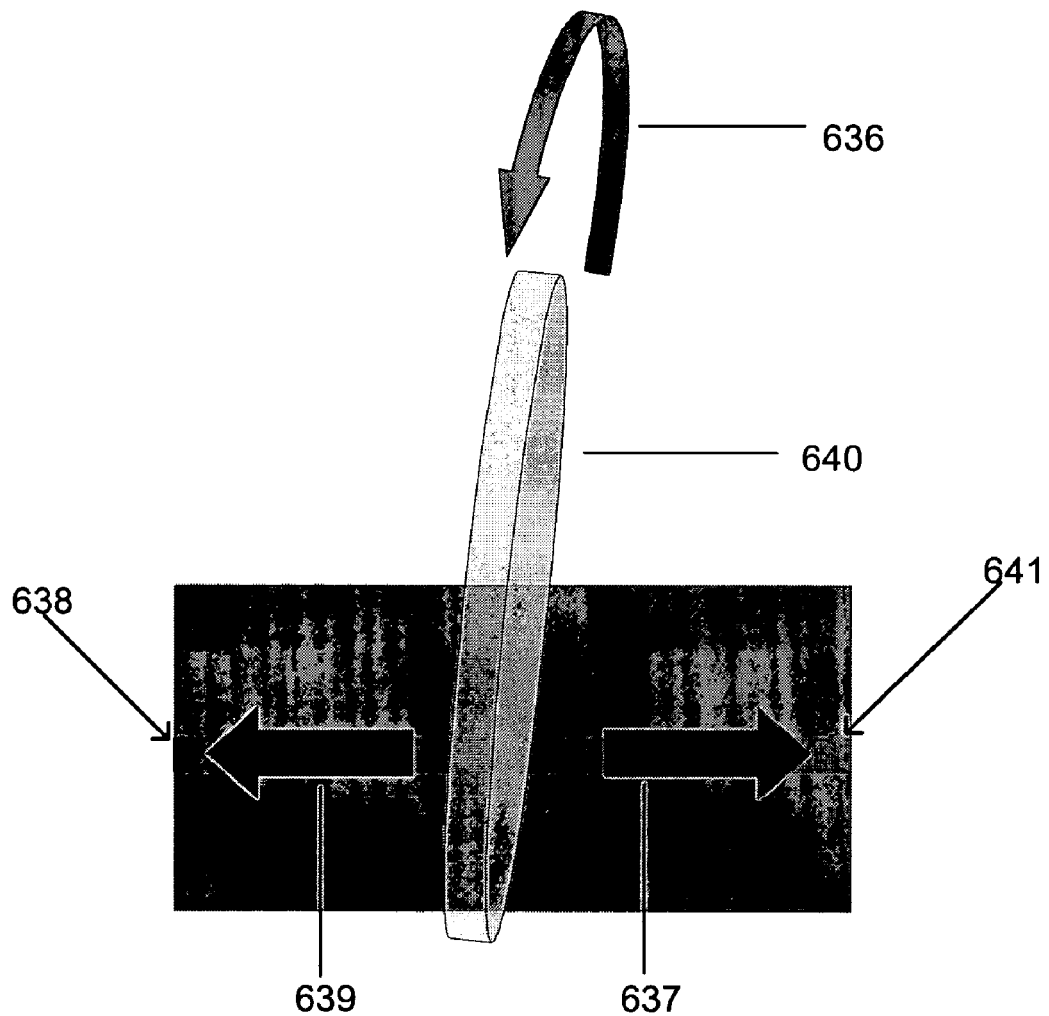
FIG. 6 illustrates a dithered point source reference scanner according to one embodiment of the present invention.

Referring now to FIG. 6, a dithered point source reference scanner is illustrated according to one embodiment of the present invention. A circular glass wedge 640 is rotated about an axis as shown by arrow 636 as a beam of light 638 is projected though it. The beam of light passes through the dithered point source reference scanner to project a reference point source of light onto the retina. The light for example, is monochromatic light in the about near infrared wavelength. As wedge 640 rotates, as indicated by arrow 636, the tilt angle introduced into the transmitted beam 639 rotates, thereby scanning the reference beam. The wedge 640 is mounted at a slight angle to the optic axis preventing ghost reflections 637 from the surface of 640 from reaching a wavefront sensor (not shown). The beam returned from the eye (not shown) passes back through the rotating wedge 636, thereby canceling the tilt introduced into the beam. The reflectance from the retina 641 is measured by a wavefront sensor.

Figure 7:
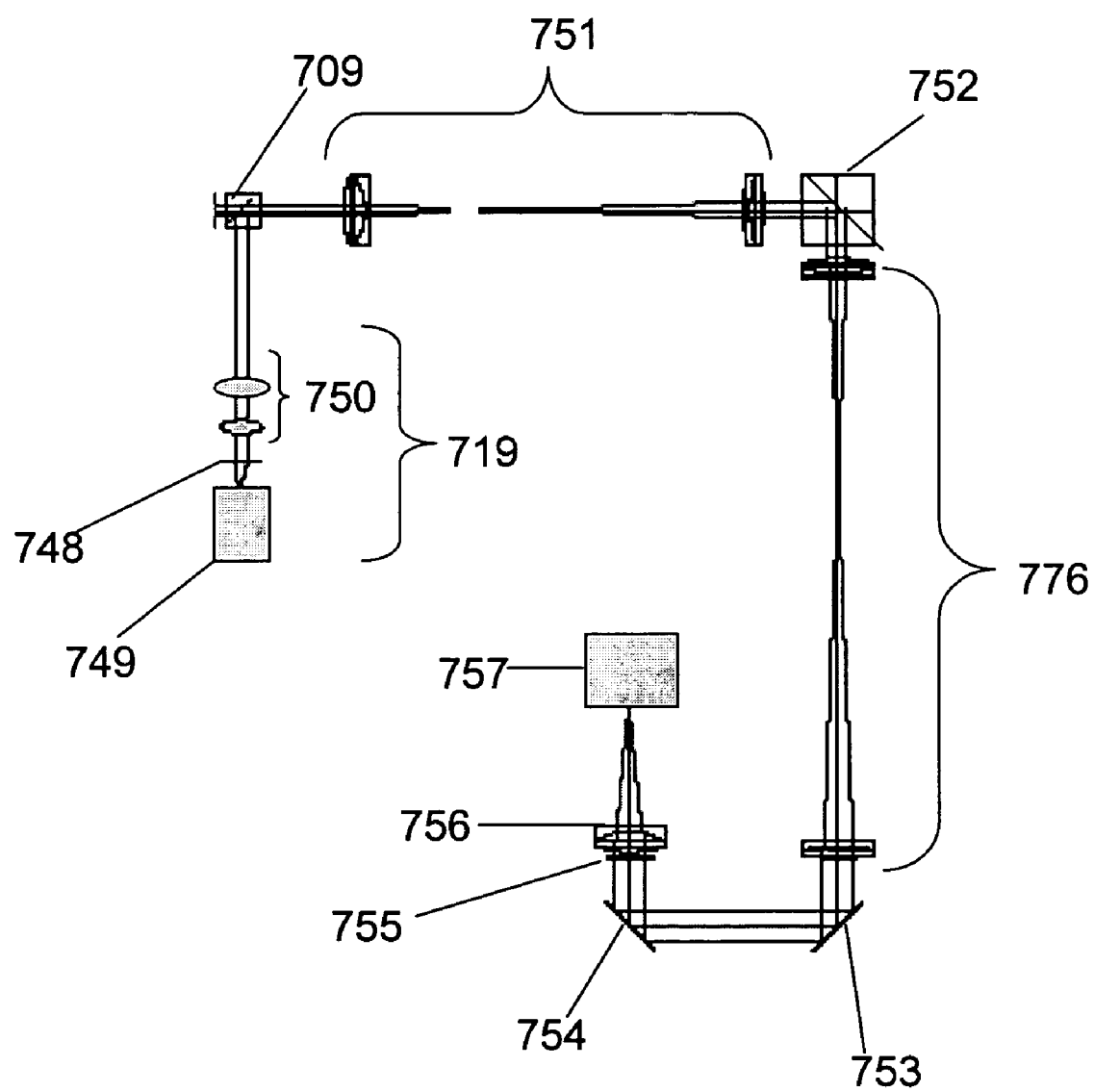
FIG. 7 illustrates an annotated ray trace passing to wavefront sensors via an optical path of an aberrometer according to one embodiment of the present invention.

Referring now to FIG. 7, interfacing of a first wavefront sensor and a second wavefront sensor with an optical path of an aberrometer is illustrated according to one embodiment of the present invention. A first wavefront sensor, for example, a distorted grating wavefront sensor comprising imaging lens 755, grating 756 with a detector 757 aligned thereto, interfaces with a second wavefront sensor, for example, a Shack Hartmann wavefront sensor 719 comprising optical relay and resizing optics 750 and lenslet array 748, with a detector aligned thereto 749, through a beam splitter 709. The beam splitter 709 directs a wavefront reflected from an eye under examination (not shown) to the wavefront sensors after passing through a polarizing beam splitter 709. The split light passes to the distorted grating wavefront sensor through relay optics 751 and resizing optics 776 that relays and resizes the system pupil to the front of the grating 755 to match the grating 755, objective lens 756, and detector 757 parameters. The reflected light from beam splitter 709 is passed through optical relay and resizing optics 750 such that the optical image of the pupil is located on lenslet array 748. Lenslet array 748 is then focused onto sensor 749. In a preferred embodiment, the optics 752, 753, 754 are folding optics that can be placed in various arrangements to package the optical layout.

According to one embodiment of the present invention, a method for measuring eye aberrations is provided. An eye under examination is aligned to an aberrometer with a fiduciary projected onto the eye. A light source projects a fiduciary onto an eye under examination. For example, the fiduciary light source emits light in the about near infrared wavelength. A detector detects the fiduciary projected onto the eye and the eye is aligned with the aberrometer. A point source reference beam illuminates an eye under examination. Dynamic range extender optics are adjusted according to a focus value for the eye under examination and/or an astigmatism value for the eye under examination. A wavefront is detected and measured by a wavefront sensor and processor. Wave aberrations for the eye under examination are characterized.

The method further comprises providing a virtual target to the eye under examination. The virtual target is generated by a scene generator via a variable accommodation mechanism to measure an eyes ability to accommodate in response to a virtual target whose apparent distance is dynamically changing. A scene generator of the variable accommodation mechanism introduces a virtual target image into the optical path for the eye to focus upon. The position of the virtual target is varied. An eye's ability to accommodate to the different focus lengths is often affected by drugs or injury. Therefore measuring an eyes variable accommodation is a useful measurement for research and treatment.

EXAMPLES

Figure 8:
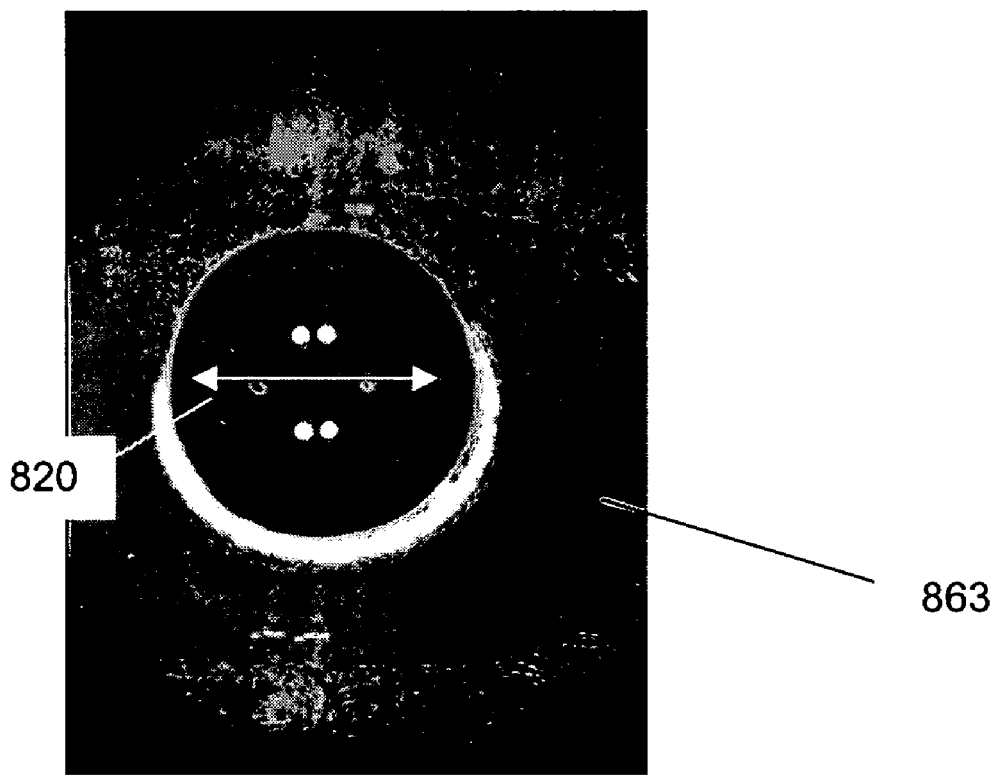
FIG. 8 illustrates an image of an infrared illuminated eye as imaged by an infrared detector for measuring the pupil size according to one embodiment of the present invention.

Referring now to FIG. 8, an image of an eye 863 and pupil 820 as seen through a near infrared detector is illustrated according to one embodiment of the present invention. Pupil diameter as illustrated by the double head arrow. The diameter is a value used for reducing the data and comparing subject data according to one embodiment of the present invention. An infrared light source (not shown) illuminates an eye and the illuminated eye is detected with an infrared detector (not shown). For example, the light source comprises an infrared diode that operates in the short wave infrared, such as at about 900 nm. The wavelength is invisible to the subject but readily observable with an infrared detector such as a CCD type of camera with an objective lens. The diameter of the pupil is determined for example by measuring the number of pixels of the detector across which the pupil diameter spans.

Figure 9:
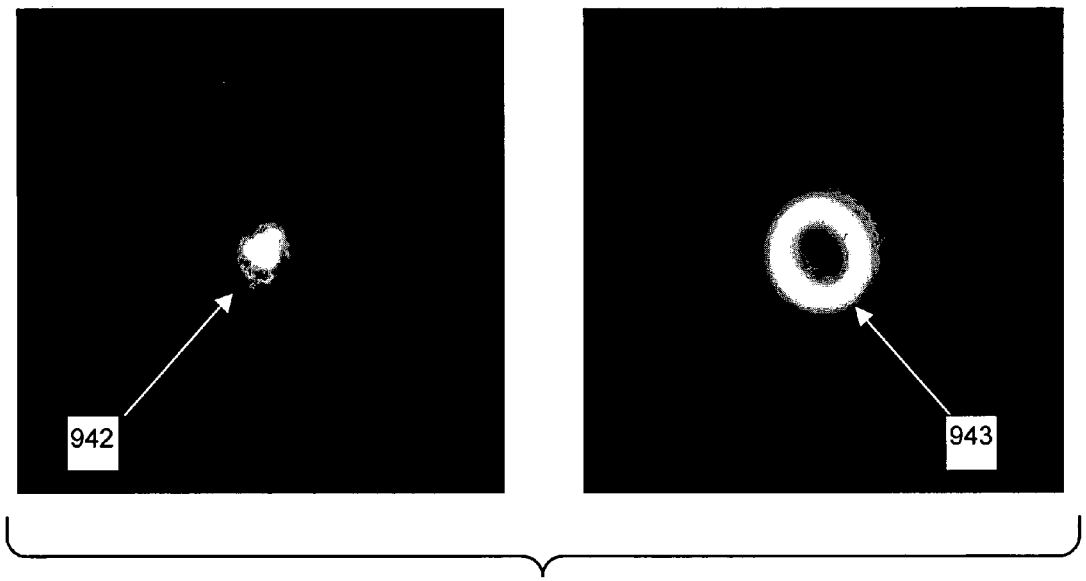
FIG. 9 illustrates a static point source reference and a dithered point source reference according to one embodiment of the present invention.

Referring now to FIG. 9, a reference beam on the retina is illustrated for a static reference 942 and a dithering reference 943 is illustrated according to one embodiment of the present invention. A reference beam passes through a dithered point source reference scanner (not shown) providing a circular doughnut type of image 943 on a retina. The size of the circular spot is selected to be smaller than the isoplanatic angle of the aberrations in the eye and is rotated fast enough to be faster than the Greenwood frequency of the aberrations in the eye, and to appear as a point element to the detectors used in the wavefront systems. A transmissive dithering point source scanner allows non rotating measurements to be made, for example by eliminating the rotation of the wedge.

A reference spot within the eye pupil obtained with a wavefront sensor having a dithered point source reference, according to one embodiment of the present invention, provides well formed spots. The resulting image lacks the amplitude variations common to Hartmannogramms obtained with a static reference. The image is acquired with a single exposure of about 30 msec thereby eliminating the need to take multiple images and average the images or a single image over a greater time course. The image acquisition rate can be increased by decreasing the exposure time.

Figure 10:
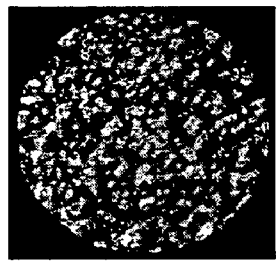
FIG. 10 illustrates an example of an image of a static point source reference after propagating through the eye.
Figure 11:
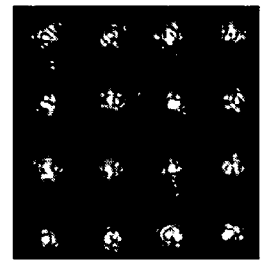
FIG. 11 illustrates a Hartmannogramm corresponding to FIG. 10.

Referring now to FIG. 10, the reflected image of a static reference point source provided to an eye under examination is illustrated. Referring now to FIG. 11, a Hartmannogram corresponding the intensity distribution illustrated in FIG. 10 is illustrated. The spot shapes on the Hartmannogram are very irregular, which makes the error of estimations of the spots' centers rather large.

Figure 12:
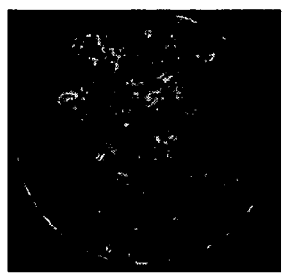
FIG. 12 illustrates an example of an image of a dithered point source reference after propagating through the eye.
Figure 13:
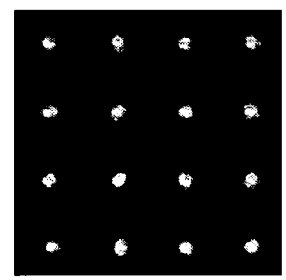
FIG. 13 illustrates a Hartmannogramm corresponding to FIG. 12.

Referring now to FIG. 12, the reflected image of a dithering reference point source provided to an eye under examination is illustrated. Referring now to FIG. 13, a Hartmannogram corresponding to the intensity distribution shown in FIG. 12 is illustrated. The spot shapes on the Hartmannogram are more regular and have a Gaussian distribution with a well defined centroid. This improvement in the energy distribution within the spot increases the accuracy of the estimation of the centroid used in wavefront reconstruction by more than 10 times. A dithered reference reduces the speckle modulation. The Hartmannogramm in FIG. 11 and FIG. 13 were taken with the same exposure, detector, lenslet array and settings.

According to one embodiment of the present invention, wavefront data is collected at a higher rate of acquisition than previously reported since a single image provides improved data. According to one example, data is collected at 70 frames per second providing usable frequency data at over 20 Hz. A high rate of data acquisition provides for improved tracking of the time varying magnitudes of aberrations and to process the data using standard statistic techniques to locate frequency dependent features. According to another embodiment, aberration frequency signatures of between about 3-15 Hz are measured. According to yet another embodiment, frequency signatures of between about 18-30 Hz are measured. According to yet another embodiment, frequency signatures of greater than about 30 Hz are measured. Frequency signatures of aberrations correlate to neurologic and physiologic function or dysfunction. For example changes in heart rate and ocular motor injury are known to correlate with the frequency of aberrations found in the eye.

In yet another embodiment of the present invention, the system and method operates manually. In an alternative embodiment, the present invention operates automatically with various general purpose computers. For example a computer controls detectors, recording outputs and results from the detectors, (both raw and calculated results) as well as dynamic focus extender optics, astigmatism extender optics and variable accommodation optics.

Alternate embodiments will be apparent to those skilled in the art with other types of equipment that record the necessary images may be employed and related statistical and analysis techniques may be used without departing from the scope of the invention as claimed. Further, the embodiments and examples described herein are illustrative only and are not meant as limitations on the claims hereof.

We claim:

1. An ophthalmic aberrometer comprising:
   a single distorted grating wavefront sensor aligned with an eye through an optical path;
   a light source for introducing a light beam into the eye via the optical path;
   the optical path comprising: a point source from which the light beam emanates before passing to a retina of the eye to form a point source reference mark on the retina; and
   wherein the single distorted grating wavefront sensor is positioned to measure the variation in the curvature of the wavefront reflected from the retina of the eye via the optical path.

2. The ophthalmic aberrometer of claim 1, wherein the light source for introducing a light beam is a monochromatic source.

3. The ophthalmic aberrometer of claim 1 further comprising:
   a near infrared light source for illuminating the eye and a near infrared detector for detecting the illuminated eye.

4. The ophthalmic aberrometer of claim 1 further comprising:
   a light source for projecting a fiduciary onto the eye and a detector for detecting the fiduciary projected onto the eye.

5. An ophthalmic aberrometer comprising:
   means for directing a light beam onto a retina of an eye under examination through an optical path wherein the optical path comprises: a point source from which the light beam emanates before passing to the retina to form a point source reference mark on the retina;
   means for directing at least a portion of the light beam reflected from the retina of the eye under examination through the optical path to a single distorted grating wavefront sensor;
   means for detecting a wavefront which is reflected from the retina of the eye via the optical path; and
   means for determining characteristics of the variation in the curvature in the wavefront detected from the single distorted grating wavefront sensor.

6. A method for determining aberrations of an eye under examination comprising:
   directing a light beam onto a retina of the eye under examination through an optical path wherein the optical path comprises: a point source from which the light beam emanates before passing to the retina to form a point source reference mark on the retina;
   directing at least a portion of the light beam reflected from the retina of the eye under examination through the optical path to a single distorted grating wavefront sensor;
   detecting a wavefront which is reflected from the retina of the eye via the optical path; and
   determining characteristics of the variation in the curvature in the wavefront detected from the single distorted grating wavefront sensor.

7. The method of claim 6 further comprising:
   projecting a fiduciary onto the eye to align the eye with an aberrometer.

8. The method of claim 6 further comprising:
   measuring a pupil of the eye under examination.

9. The method of claim 6 further comprising:
   varying an apparent distance of a virtual target while the eye under examination is focused upon the virtual target.

10. A method for analyzing aberrations in an eye having aberration frequency signatures with an aberrometer comprising:
    directing a light beam onto a retina of the eye under examination through an optical path, the optical path comprises: a point source from which the light beam emanates before passing to the retina to form a point source reference mark on the retina;
    directing at least a portion of the light beam reflected from the retina of the eye through the optical path to a single distorted grating wavefront sensor; and
    determining frequency characteristics measured from variation in the curvature in the wavefront detected from the single distorted grating wavefront sensor of aberrations having frequency signatures.

11. A method for measuring with an aberrometer an eye's dynamic accommodation in response to a virtual moving target comprising:
    directing a light beam onto a retina of the eye under examination through an optical path wherein the optical path comprises: a point source from which the light beam emanates before passing to a retina to form a point source reference mark on the retina,
    directing at least a portion of the light beam reflected from the retina of the eye under examination through the optical path to a distorted grating wavefront sensor;
    varying an apparent distance of a virtual target while the eye under examination is focused upon the virtual target;
    detecting a wavefront which is reflected from the retina of the eye via the optical path; and
    determining characteristics of the wavefront detected.

12. The method of claim 11 wherein determining characteristics of the wavefront detected comprises determining frequency characteristics of aberrations having frequency signatures.

* * * * *